(12) United States Patent
Kurt et al.

(10) Patent No.: US 7,118,659 B2
(45) Date of Patent: Oct. 10, 2006

(54) ROBOTIC FRIENDLY EXTERNAL LOADING SYSTEM FOR ELECTROPHORESIS INSTRUMENT AND METHOD

(75) Inventors: Thomas J. Kurt, Ames, IA (US); Kevin C. Kennedy, Kelley, IA (US)

(73) Assignee: Combisep, Inc., Ames, IA (US)

( * ) Notice: Subject to any disclaimer, the term of this patent is extended or adjusted under 35 U.S.C. 154(b) by 571 days.

(21) Appl. No.: 10/375,790

(22) Filed: Feb. 27, 2003

(65) Prior Publication Data

US 2004/0168919 A1 Sep. 2, 2004

(51) Int. Cl.
*G01N 27/447* (2006.01)
*G01N 27/453* (2006.01)

(52) U.S. Cl. ...................... 204/451; 204/601
(58) Field of Classification Search ........ 204/451–455, 204/601–604
See application file for complete search history.

(56) References Cited

U.S. PATENT DOCUMENTS

| | | | | |
|---|---|---|---|---|
| 4,827,780 | A | * | 5/1989 | Sarrine et al. ............ 73/864.21 |
| 5,508,197 | A | * | 4/1996 | Hansen et al. ............ 435/285.1 |
| 5,582,705 | A | | 12/1996 | Yeung et al. |
| 5,695,626 | A | | 12/1997 | Yeung et al. |
| 5,741,411 | A | | 4/1998 | Yeung et al. |
| 5,900,934 | A | | 5/1999 | Gilby et al. |
| 6,027,627 | A | * | 2/2000 | Li et al. ...................... 204/603 |
| 2002/0150450 | A1 | * | 10/2002 | Bevirt et al. ............ 414/225.01 |
| 2004/0110923 | A1 | * | 6/2004 | Moore et al. ............... 530/350 |
| 2004/0173460 | A1 | * | 9/2004 | Yamamoto et al. ......... 204/601 |

FOREIGN PATENT DOCUMENTS

| | | |
|---|---|---|
| DE | 3712776 A1 | 4/1986 |
| EP | 0 581 984 A1 | 2/1994 |
| JP | 10-206384 A * | 8/1998 |
| WO | WO 01/18528 A1 | 3/2001 |
| WO | WO 02/49761 A2 | 6/2002 |

OTHER PUBLICATIONS

JPO computer translation of JP 10-206384 A (Yoshihide et al.) (patent publication date Aug. 7, 1998).*
PCT Notification of Transmittal of the International Search Report and Written Opinion of the International Searching Authority, or the Declaration (for co-pending PCT/US2004/004469).
Kheterpal et al., "Capillary Array Electrophoresis DNA Sequencing", Analytical Chemistry News & Features 31-37 (1999).
Shi et al., "Radial Capillary Array Electrophoresis Microplate and Scanner for Hi-Performance Nucleic Acid Analysis", Anal. Chem 71:5354-5361 (1999).
Wu et al., "Absorption Spectra and Multicapillary Imaging Detection for Capillary Isoelectric Focusing Using a Charge Coupled Device Camera", Analyst, May 1995, vol. 120, pp. 1567-1571.

* cited by examiner

*Primary Examiner*—Alex Noguerola
(74) *Attorney, Agent, or Firm*—McKee, Voorhees & Sease, P.L.C.

(57) ABSTRACT

An electrophoresis instrument for analyzing multiple samples having a loading system. The loading system having a carriage moveable between an external station and a sampling station. The carriage having at least one tray upon the carriage. The sampling station being adapted for sampling the tray by an array of capillary tubes.

20 Claims, 14 Drawing Sheets

ROBOTIC FRIENDLY EXTERNAL LOADING SYSTEM FOR ELECTROPHORESIS INSTRUMENT AND METHOD

TECHNICAL FIELD OF THE INVENTION

This invention relates generally to a multiplexed, absorbance-based capillary electrophoresis system. Specifically, the invention relates to a robotic friendly external loading system for the electrophoresis system and method of using it.

BACKGROUND OF THE INVENTION

The rapid development of biological and pharmaceutical technology has posed a challenge for high-throughput analytical methods. For example, current development of combinatorial chemistry has made it possible to synthesize hundreds or even thousands of compounds per day in one batch. Characterization and analysis of such huge numbers of compounds has created a bottleneck. Parallel processing (i.e., simultaneous multi-sample analysis) is a natural way to increase the throughput. However, due to limitations related to column size, pressure requirements, detector and stationary phase materials, it is very difficult to build a highly multiplexed high-performance liquid chromatography (HPLC) system. The same goes for building a highly multiplexed gas chromatography (GC) system.

High performance capillary electrophoresis (CE) has rapidly become an important analytical tool for the separation of a large variety of compounds ranging from small inorganic ions to large biological molecules. To perform a conventional separation, a capillary tube is filled with a buffer solution, a sample is loaded into one end of the capillary tube, both ends of the capillary tube are immersed in the buffer solution and a large potential is applied across the capillary tube. The sample components are separated electrophoretically as they migrate through the capillary tube.

CE is used for general separations, enantiomeric separations, the peptide mapping of proteins, amino acid analysis, nucleic acid fractionation and the quantitative measurement of acid dissociation constants ($pK_a$ values) and octanol-water partition coefficients (log $P_{ow}$ values). What all these applications have in common is the measurement of the mobility of chemical species in a capillary tube.

With attractive features such as rapid analysis time, high separation efficiency, small sample size, and low solvent consumption, CE is increasingly used as an alternative or complimentary technique to HPLC. For example, the use of capillary gel electrophoresis has greatly improved DNA sequencing rates compared to conventional slab gel electrophoresis. Part of the improvement in speed, however, has been offset by the inability to accommodate multiple lanes in a single run that is inherent in slab gels. Highly multiplexed capillary electrophoresis, by making possible hundreds or even thousands of parallel sequencing runs, represents an attractive approach to overcome the current throughput limitations of existing DNA sequencing instrumentation. Such a system has been disclosed in U.S. Pat. No. 5,582,705 (Yeung et al.), U.S. Pat. No. 5,695,626 (Yeung et al.) and U.S. Pat. No. 5,741,411 (Yeung et al.). In this system, a fluorescent sample is separated by electrophoresis inside a capillary tube. A laser irradiates one section of the capillary tube. When the sample component migrates through the irradiated portion of the tube, the fluorescence emission is detected by an optical detector.

While fluorescence detection is suitable for DNA sequencing applications because of its high sensitivity and special labeling protocols, many samples of interest do not fluoresce. UV absorption detection is useful because of its ease of implementation and wider applicability, especially for the deep-UV (200–220 nm) detection of organic and biologically important compounds. In a UV detection system, a section of capillary tube is irradiated with a UV light source. A photodetector detects the light that passes through the tube. When a UV absorbing sample component passes through the irradiated portion of the capillary tube, the photodetector detects less passed light (indicating absorbance). In this way an electropherogram, a plot of absorbance versus time, can be produced.

A capillary isoelectric focusing system using a two-dimensional charge-coupled device (CCD) detector, in which one dimension represents the capillary length and the other dimension records the absorbance spectrum, has been described by Wu and Pawliszyn, *Analyst* (Cambridge), 120, 1567–1571 (1995). The system has been used with two capillary tubes, but is not easily adapted for three or more capillary tubes because the system requires the capillary tubes to be separated by space. Instead of providing wavelength resolution in the second CCD dimension, isoelectric focusing in two capillary tubes is simultaneously monitored. The use of optical fibers for illumination, however, has led to low light intensities and poor UV transmission. So, only visible wavelengths have been employed for the detection of certain proteins. Because the CCD has a very small electron well capacity (about 0.3 million electrons), the limit of detection (LOD) of this system is limited by the high shot noise in absorption detection. The use of the CCD produces an overwhelming amount of data per exposure, limiting the data rate to one frame every 15 seconds. Also, the imaging scan utilized is not suitable for densely packed capillary arrays because of the presence of mechanical slits to restrict the light paths. Further, in order to avoid cross-talk, only square capillary tubes can be used.

Photodiode arrays (PDA) are used in many commercial CE and HPLC systems for providing absorption spectra of the analytes in real time. Transmitted light from a single point in a flow stream is dispersed by a grating and recorded across a linear array. A capillary zone electrophoresis system using a photodiode array as an imaging absorption detector has been described by Culbertson and Jorgenson, Anal. Chem., 70, 2629–2638 (1998). Different elements in the array are used to image different axial locations in one capillary tube to follow the progress of the separation. Because the PDA has a much larger electron well capacity (tens of millions of electrons), it is superior to the CCD for absorption detection. Time-correlated integration is applied to improve the signal-to-noise ratio (SIN).

Gilby described an absorption detection approach for the simultaneous analysis of multiple systems in U.S. Pat. No. 5,900,934. This system includes a photodetector array comprising a plurality of photosensitive elements connected to provide a serial output. The elements are typically pixels of a photodiode array (PDA). The elements are illuminated by a light source positioned to illuminate at least a portion of the photodetector array. The light source may be an AC or DC mercury lamp or other useable light source for chromatography. An array of separation channels is disclosed between the light source and the photodetector array, each of the separation channels having a lumen, a sample introduction end and a detection region disposed opposite the sample introduction end. The array is a multiple parallel capillary electrophoresis system. A mask element having at least one aperture for each associated separation channel is required. Each aperture corresponds to its associated separation channel, thereby selectively permitting light from the light source to pass through the lumen of its associated separation channel. At least a portion of the light passing through the lumen of the associated separation channel falls on the respective photo sensitive element of the photo detector array to effect measurement of absorption of light by a sample introduced into the sample introduction end of the associated separation channel.

The system described by Gilby et al. has disadvantages because it limits the amount of light impinging on the separation channel, providing less than desirable light intensity to the PDA. Further, aligning the apertures and the mask elements with the separation channels, e.g., capillary tubes, is difficult for several reasons. For example, positioning the capillary tubes with equal separation there between is difficult as the capillary tubes are generally not of equal dimension, e.g., diameter tolerances very greatly. Further, for example, the mask geometry does not provide identical light paths, which leads to non-linear response. Also, a mask can produce stray light, which leads to poor detection limits, and does not completely eliminate cross-talk from the adjacent capillary tubes, since the light beams are diverging and cannot escape the detector element. In addition, a mask can be difficult to manufacture, due to the requirement of uniformity. Also, Gilby places the sample and the PDA too close together, resulting in stray light, cross-talk and the inability to use the maximum path length of light.

Yeung et al., in PCT Application WO 01/18528A1, disclosed a multiplexed, absorbance-based capillary electrophoresis system for analyzing multiple samples simultaneously, without use of a mask or slit, comprising a light source, a planar array of capillary tubes and a detector positioned on-axis with the light source and positioned on-axis with and parallel to the planar array of capillary tubes at a distance of at least about 10 times a cross-sectional distance of a capillary tube measured orthogonally to the planar array of multiple capillary tubes.

The system described by Yeung et al. works, but has disadvantages. In Yeung's system, the detector is positioned on-axis with the light source. Therefore, light that passes between the capillary tubes and light that passes through the capillary tubes (and samples) both strike the detector. The light that passes between the capillary tubes is not of interest since it represents a measurement of nothing, but provides a peak that is registered by the detector and recorded by the associated software. It is preferable that light that passes between the capillary tubes never reaches the detector.

In addition, the rate of sample migration in the system described by Yeung et al. is slower than ideal, especially when performing some types of separations employing high current generating buffers. This is due to the fact that the high currents generated by some buffers lead to excessive joule heating in the capillary array, which can degrade the quality and reproducibility of the separation. In such situations it is necessary to lower the operating voltage, resulting in increased analysis times. An approach is therefore desired in these situations to improve the analysis time.

Some applications described by Yeung et al. using Yeung's system, while novel, are limited due to the fact that all separations utilize the same buffer for the outlet and the inlet reservoirs. While Yeung has simultaneously performed separations using different buffers in different capillary tubes of an array, the outlet ends of the capillary tubes were bundled separately and separate buffer reservoirs were used for each different buffer. This approach also required the filling of the different capillary bundles individually by hand with a syringe which is not practical from an automation or ease of use standpoint.

In summary, while other multiplexed, absorbance-based capillary electrophoresis systems exist, there is a need for an instrument such that separations can be performed at a faster rate and in an automated fashion.

The primary objective of this invention is to fulfill the above described needs with an improved multiplexed, absorbance-based capillary electrophoresis system.

These and other objects, features and/or advantages of the present invention will become apparent from the specification and claims.

SUMMARY OF THE INVENTION

The foregoing objective may be achieved by an electrophoresis instrument. The instrument has an instrument body with a carriage attached moveable between an external station and a sampling station. The carriage has at least one tray upon the carriage. The instrument has an array of capillary tubes attached to the instrument body sampling the tray at the sampling station. The instrument additionally has a photodetector for detecting light passing through the capillary tubes and a light source attached to the instrument body positioned with respect to the photodetector.

The foregoing objectives may further be achieved by a loading system for an electrophoresis instrument. The loading system has a carriage moveable between an external station and a sampling station. The carriage has least one tray upon the carriage. The sampling station being adapted for sampling the tray by an array of capillary tubes.

The foregoing objectives may still further be achieved by a method of using an electrophoresis instrument with a loading system. The method has the step of loading at least one tray upon a carriage at an external station. The method also having the steps of moving the carriage from the external station to a sampling station and then sampling the tray with an array of capillary tubes. The method also having the steps of emitting light from a light source directed through the array of capillary tubes and then detecting light passing through the capillary tubes with a photodetector.

DETAILED DESCRIPTION OF A PREFERRED EMBODIMENT OF THE INVENTION

Figure 1:
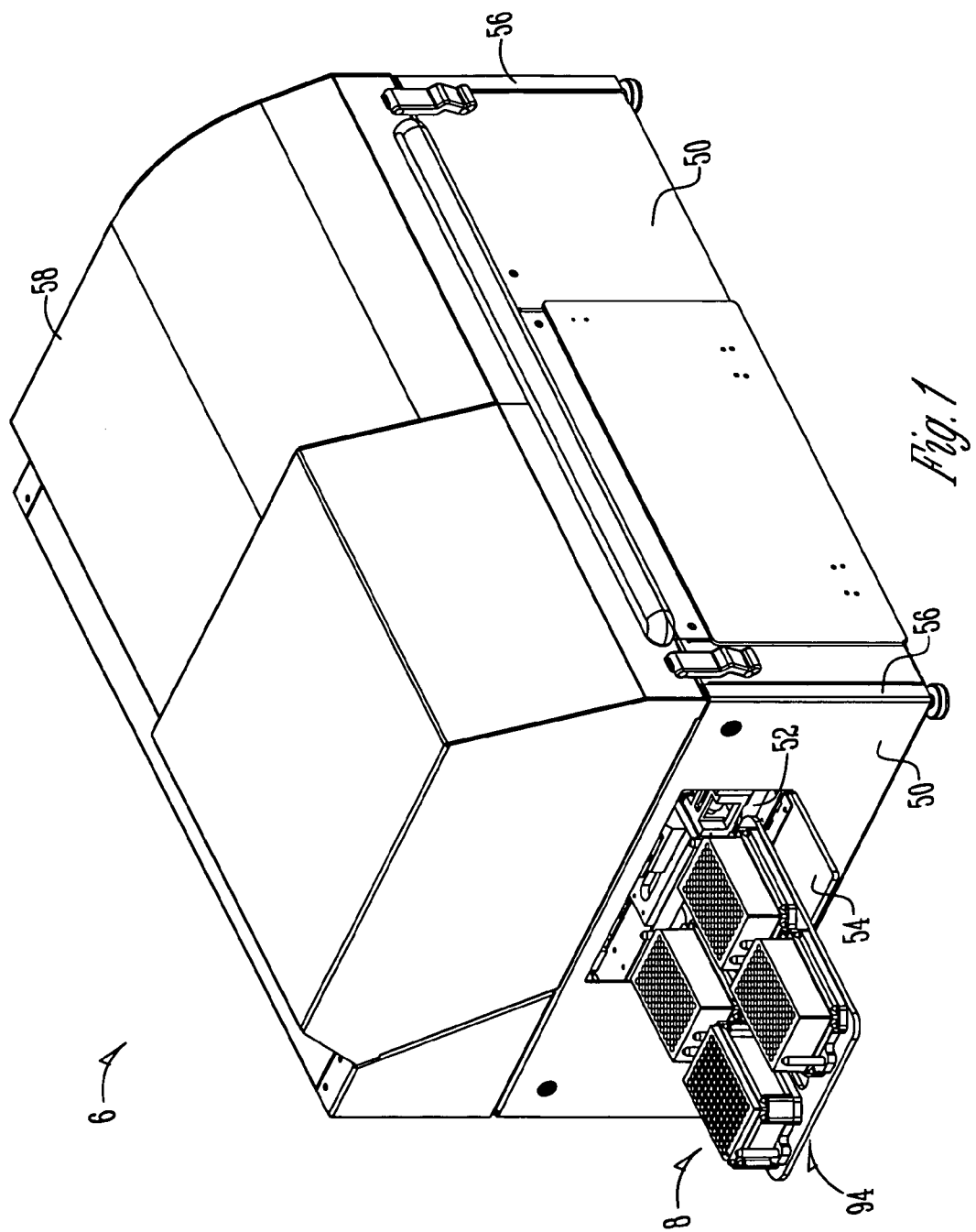
FIG. 1 presents a perspective view of the electrophoresis instrument having a loading system in an external station.

The invention, as hereinbefore explained, is a multiplexed, absorbance-based electrophoresis system having a robotic friendly loading system. The invention system and method are for the separation, detection and identification of chemical species enhanced by a loading system. Referring to FIG. 1, 6 designates the electrophoresis instrument with a loading system 8.

FIG. 1 illustrates is in the general form of the CombiSep MCE-Pro™. This model as well as other electrophoresis instruments may be used in applications such as combinatorial chemistry including compound development using high throughput screening technologies; pharmaceutical/biotech discovery for analyzing compounds for purity, bioactivity, lob P, $pk_a$, composition, and DNA sizing; and proteomics and metabolomics for screening and mapping of proteins and metabolites. These electrophoresis instruments have operation modes including +/−20 kV applied voltage, constant or gradient voltage, vacuum or electrokinetic injection, and 0–60 μA per capillary. These electrophoresis instruments also have high throughput analysis because of their ability to do parallel separations through multiplexed capillary electrophoresis, through absorbance-based detection capable of detecting greater than 90% of all compounds except for simple sugars and alcohols, through stand alone operation, and through robotic interface capabilities. These electrophoresis instruments have reagent kits including: log P/$pk_a$ chiral analysis, purity screening, DNA sizing, and peptide analysis. The electrophoresis instruments also include buffer and rinse capabilities which clean and condition the instrument through software controlled cycles. The electrophoresis instruments are also capable of data collection through a workstation I/O with network capabilities.

Figure 2:
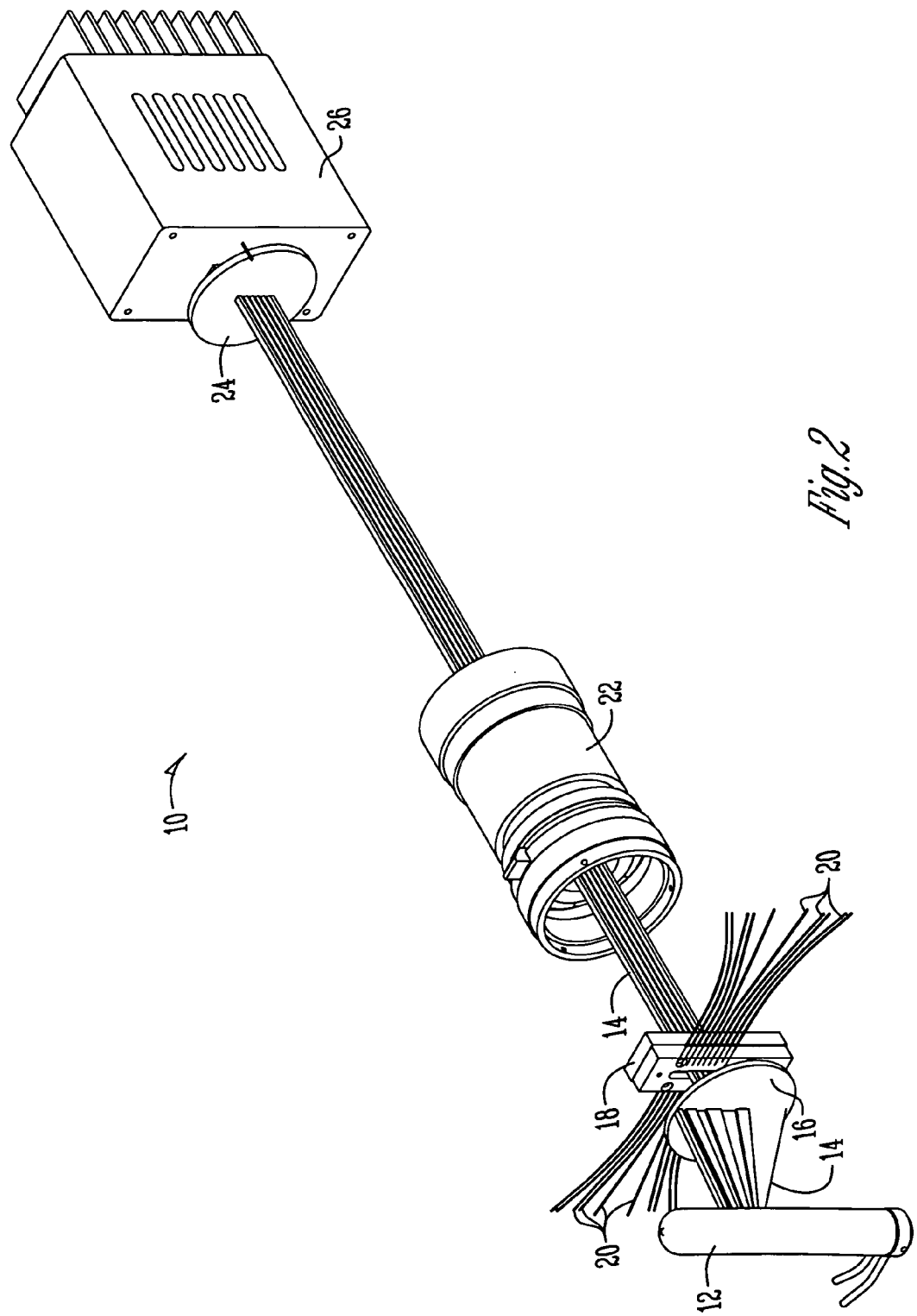
FIG. 2 presents a schematic diagram of the absorbance-based capillary electrophoresis system.

Referring to FIG. 2, 10 designates the absorbance-based capillary electrophoresis system. The light beam 14 originates in the light source 12 and then travels through the collimating lens 16, the planar array of capillary tubes 20, the flat-field lens 22, the optical filter 24 and is collected in the detector 26. The array block 18 holds the capillary tubes 20 in place.

The distance between the area where light is emitted from the light source 12 and the planar array of capillary tubes 20 is not critical to the practice of the present invention. However, the shorter the distance between the area where light is emitted from the light source 12 and the planar array of capillary tubes 20, the more light is received by the planar array of capillary tubes 20. The more light that the planar array of capillary tubes 20 receives, the more sensitive is the detection. The greater the distance between the area where light is emitted from the light source 12 and the planar array of capillary tubes 20, the more uniform is the light received by the planar array of capillary tubes 20.

Preferably, the distance between the planar array of capillary tubes 20 and the detector 26 is at least about 10 times, more preferably, at least about 100 times, a cross sectional distance of a capillary tube 20 measured orthogonally to the plane of the planar array of capillary tubes 20. The critical feature is that the distance must be such that the entire array is visible and in focus. Thus, the distance between the planar array of capillary tubes 20 and the detector 26 is preferably from about 1 centimeter to about 100 centimeters, more preferably from about 3 centimeters to about 40 centimeters, and most preferably from about 20 centimeters to about 40 centimeters.

The outlet ends of the capillary tubes 20 are immersed in a buffer solution and operatively connected to a vacuum source, such as a pump, rather than solely immersed in a buffer solution. By applying vacuum in addition to voltage during a separation, the analysis time can be significantly reduced as compared to using only voltage to impart a separation.

Figure 3:
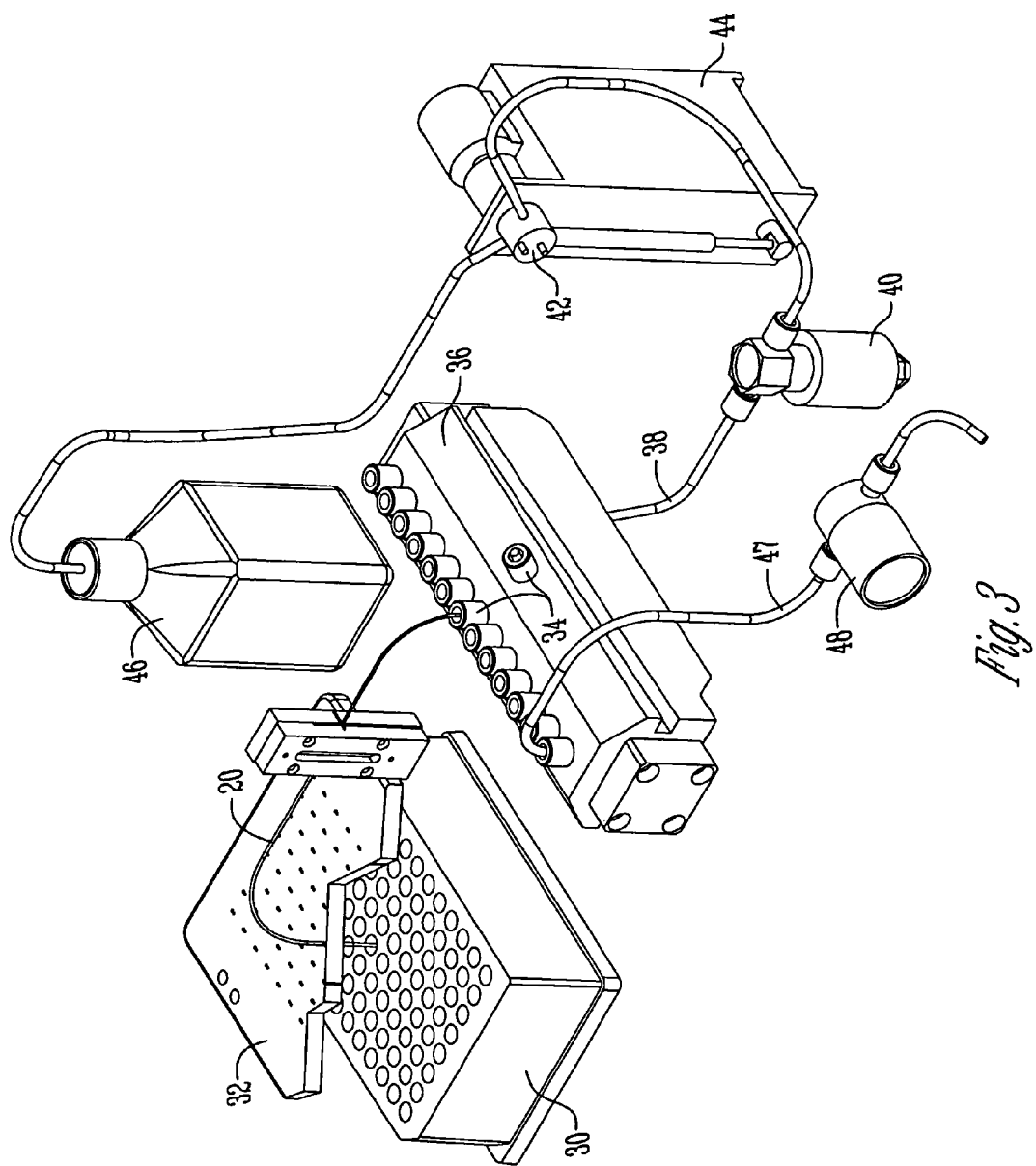
FIG. 3 presents a schematic diagram of the components comprising the vacuum assistance system of the invention.

FIG. 3 illustrates a preferred set-up for vacuum mediated capillary electrophoresis. Only one capillary tube 20 is shown for clarity. The inlet end of the capillary tube 20 is immersed in a buffer solution in a tray 30. The tray may consist of from 1 to 96 separate reservoirs, which mate with the capillary tubes 20 of the array. Above the tray 30, the capillary tube 20 is supported by a circuit board or input plate 32.

The circuit board 32 is also where an electrical connection is made to the capillary tube 20. The capillary tube 20 next passes through the array block 18 and then into a fitting 34 connected to a reservoir manifold 36. The outlet ends of the capillary tubes 20 are fastened to the reservoir manifold 36 in a manner that creates an airtight seal so that pressure or vacuum can be applied to the capillary tubes 20 and so that the capillary tube 20 ends make contact with the outlet buffer solution in the reservoir manifold 36. Inside the reservoir manifold 36, a second electrical connection is made to the capillary tube 20 and all the capillary tubes 20 are combined into one outlet tube 38 that exits the reservoir manifold 36 through another fitting 34. The outlet tube 38 passes through a pressure transducer 40 and then feeds into a multiport valve 42 connected to a vacuum pump 44. The multiport valve 42 is not essential here. The vacuum pump 44 can connect to the reservoir manifold 36 directly. The multiport valve 42 is used for buffer solution selection only. The vacuum pump preferably provides a small level of vacuum. Examples of suitable vacuum pumps include syringe pumps or diaphragm pumps. A syringe pump is preferred because the syringe plunger movement speed and distance can be concisely computer controlled. When the syringe plunger is pulled a small distance, a small level of vacuum is created. The outlet tube 38 then continues from the multiport valve 42 and terminates at a waste container 46. The vent tube 47 connects a vent valve 48 to the reservoir manifold 36. In operation, buffer solution is continually pumped from the tray 30 through the system to the syringe until it is full and then into a waste container while the vent valve 48 is at closed position. The output signal from the pressure transducer 40 is monitored by a computer so that the vacuum level is continuously monitored. When the vacuum level exceeds the preset level, e.g. −0.1 psi, the computer turns off the vacuum pump. However, when the vacuum level falls below the preset level due to solution movement from the capillary tubes 20 into the reservoir manifold 36, the computer turns on the vacuum pump to maintain the appropriate vacuum level. Therefore a constant vacuum level to the reservoir manifold 36 is maintained during the entire separation period. All capillary tubes 20 that connect to the reservoir manifold 36 will face the same vacuum level. The vacuum level is preferred to be from −0.01 to −2 psi. Too high of vacuum levels will move the samples to the detection windows of the capillary tubes 20 too quickly to obtain reasonable separation.

Another novel feature of the proposed invention is that a different buffer can be used in each capillary tube 20 and its associated inlet reservoir (for example, up to 96 different running buffers if 96 capillary tubes and 96 separate inlet reservoirs are used in a tray 30), with a single, common outlet reservoir manifold 36. The outlet reservoir manifold 36 is initially filled with a common buffer or water. The individual capillary tubes 20 can then be filled from the inlet side with buffer either electrophoretically or by applying vacuum. Using different buffers in different capillary tubes 20 in conjunction with a common reservoir manifold 36 can result in a substantial decrease in reagent costs as expensive buffer additives need only be added to the tray 30.

The reservoir manifold 36 is preferably made of an inert material such as polytetrafluoroethylene, polyethylene, polypropylene or polyethylene terephthalate.

By "capillary tubes" 20 is meant at least 3 or more, preferably at least about 10, more preferably at least about 90, and desirably as many as can be accommodated by the system described herein. The capillary tubes 20 allow the passage of light from the light source 12 through the walls of the capillary tubes 20 facing the light source 12, through the samples in the capillary tubes 20, and through the walls of the capillary 20 tubes facing the detector 26. Thus, the walls of the capillary tubes 20 are desirably transparent, although, in some instances, the walls of the capillary tubes 20 can be translucent. It is not necessary for the entirety of the walls of the capillary tubes 20 to allow the passage of light from the light source 12 as described above as long as at least a portion of walls of the tubes allow the passage of light from the light source 12 such that the samples in the capillary tubes 20 are irradiated and light that is not absorbed by the absorbing species and the samples is detectable by the detector 26.

In general, the capillary tubes 20 should have smooth surfaces and uniformly thick walls and be made of a material transparent over the range of wavelengths of light absorbed by an absorbing species in the sample, the absorbance of which is to be detected or measured. Preferred materials for capillary tubes 20 include, but are not limited to, plastics, quartz, fused silica and glass. The cross-section of a capillary tube 20 is not critical to the present invention. However, the smaller the cross-section of the capillary tube 20, the more useful is the capillary tube 20 in highly multiplexed applications as a greater number of capillary tubes 20 can be used in a smaller amount of space. Similarly, the thickness of a walls of the capillary tubes 20 is not critical to the present invention. The walls should be of sufficient thickness as to maintain the structural integrity of the capillary tube 20, yet not so thick as to adversely impede the passage of light through the capillary tube 20. The shape of the capillary tube 20 also is not critical to the present invention. The capillary tube 20 can have any suitable shape. However, the preferred size and shape of the capillary is 150 μm outside diameter, 75 μm inside diameter and circular in shape. Desirably, the shape of the capillary tube 20 is conducive to being closely packed and minimizes the generation of stray light by the container. The capillary tubes 20 are preferably from about 10 cm to about 200 cm long.

Capillary tubes 20 are commercially available by a number of sources including Polymicro Technologies, Inc., Phoenix, Ariz. The capillary tube 20 is preferably coated with a polymer such as polyimide so that it is mechanically stable. The coating must be removed in the region to be irradiated by the light source 12. An excimer laser can be used to remove the polymer coating.

Preferably, the capillary tubes 20 in the planar array are arranged substantially parallel and adjacent to each other. Adjacent capillary tubes 20 can be physically touching each other along all or a portion of their lengths, although slight inconsistencies in capillary wall diameter or other features of the array can prevent them from being in contact along their entire lengths. The planar array of capillary tubes 20 desirably is rigidly mounted to reduce flicker noise.

The electrical potential used for electrophoretic separation is not critical to the invention. A typical potential ranges from 5,000 to 30,000 V.

If a large amount of heat is generated during the method, particularly in the vicinity of the planar array of capillary tubes 20, cooling should be employed to dissipate the heat. Excessive heat can lead to mechanical vibrations between adjacent capillary tubes 20, which, in turn, can lead to excess noise. Fans can cool the capillary tubes 20.

The detector 26 can comprise any suitable means of detecting absorption. Preferably, the detector 26 comprises a plurality of absorption detection elements, such as a plurality of photosensitive elements, which desirably are positioned in a linear array, although a two-dimensional image array detector can be used. Desirably, the detector 26 is parallel to and in-line with a linear array of capillary tubes 20. The detector 26 is desirably rigidly mounted to reduce flicker noise.

Preferably, the detector 26 is a linear photodiode array (PDA). Desirably, the PDA incorporates a linear image sensor chip, a driver/amplifier circuit and a temperature controller, which desirably thermoelectrically cools the sensor chip to a temperature from about 0° C. to about −40° C. Lowering the temperature lowers the dark count and minimizes the temperature drift, thus enabling reliable measurements to be made over a wide dynamic range. The driver/amplifier circuit is desirably interfaced to a computer via an I/O board, which preferably also serves as a pulse generator to provide a master clock pulse and a master start pulse, which are required by the linear image sensor. The PDA records the image linearly, not two-dimensionally. Preferably, the data acquired is written directly to the hard disk in real time. Also, preferably, the signals from up to at least 10 elements of the PDA are displayed in real time.

Preferably, the PDA comprises linearly aligned pixels, in which case each capillary tube is optically coupled to less than about 10 pixels, more preferably from about 7 to about 9 pixels, some of which are coupled to the walls of the capillary and at least one of which is coupled to the lumen of the capillary. A pixel exposed to light produces an electronic signal that is proportional to the intensity of incident light.

The light source 12 preferably emits light of a wavelength in the range from about 180 nm to about 1500 nm. Examples of a suitable light source 12 include mercury (for ultra violet (UV) light absorption), tungsten (for visible light absorption), iodine (for UV light absorption), zinc (for UV light absorption) cadmium (for UV light absorption), xenon (for UV light absorption) or deuterium (for visible light absorption) lamps. Desirably, the light source 12 emits a wavelength of light that will be absorbed by the species of interest. Which wavelength of light is absorbed by the species of interest can be determined using a standard absorption spectrometer. Alternatively, spectroscopic tables that provide such information are available in the art, such as through the National Institute of Science and Technology. Desirably, a maximally absorbed wavelength of light is selected for a given species to be detected or measured such that smaller amounts of the absorbing species can be detected. The light source 12 can be a point source. Also, preferably, the light source 12 has a power output of about 0.5 mW to about 50 mW.

An optical filter 24 is desirably positioned between the planar array of capillary tubes 20 and the detector 26. The optical filter 24 prevents stray light from the outside environment from reaching the detector 26. The filter 24 passes light at and near the wavelength emitted from the light source 12 and blocks light of other wavelengths.

A flat-field lens 22 is desirably positioned between the planar array of capillary tubes 20 and the detector 26. The flat-field lens 22 couples light that is not absorbed by the one or more absorbing species in each sample with the detector 26. While a lens that is not a flat-field lens can be used in the context of the present invention, it is disadvantageous in as much as it does not image the entire field evenly. Consequently, the edges of the field are distorted and the absorption of the capillary tubes 20 positioned at the edges of the field of the lens cannot be detected or measured. The flat-field lens 22 inverts the image of the planar array onto the face of the detector 26.

A collimating lens 16 is desirably positioned between the light source 12 and the planar array of capillary tubes 20. The collimating lens 16 focuses the light from the light source 12 to irradiate the capillary tubes 20 more effectively.

While the sample can be introduced into each capillary tube 20 in a planar array of multiple capillary tubes 20 by any suitable method, preferably the samples are introduced into the capillary tubes 20 by pressure, gravity, vacuum, capillary or electrophoretic action.

The above components are placed to eliminate substantially, and desirably, completely, stray light. There are two kinds of stray light. One kind of stray light is the glare that results from the capillary tubes 20 having sidewalls and interior lumens. The other kind of stray light is that which is due to the presence of other capillary tubes 20. This kind of stray light is referred to as "cross talk." Cross talk essentially is the glare from other capillary tubes 20. Thus, there needs to be sufficient distance between the sample and the flat-field lens 22 to eliminate substantially and, desirably completely the two kinds of glare. The rate of decrease of stray light as the distance increases will eliminate most of the glare from the containers. Glare can be assessed by measuring a totally absorbing material in a container. If there is any light detected, that light is due to glare.

Preferably, raw data sets are extracted into single-diode electropherograms and analyzed by converting the transmitted light intensities collected at the detector 26 to absorbance values using a capillary tube 20 containing only buffer solution as a continuous blank reference (control). Alternatively, as many as five and preferably three adjacent diodes may be summed for each capillary tube 20 of the array to increase the overall light intensity. Root-mean-squared noise in the electropherograms is obtained using a section of baseline near one of the analyte peaks. Mathematical smoothing can be used to reduce noise significantly, without distorting the signal. In this regard, as high a data acquisition rate as possible should be employed to provide more data points for smoothing. Various algorithms including binomial, boxcar and Savitzky-Golay smoothings are preferred methods of mathematical smoothing.

As seen in FIG. 1, the electrophoresis instrument 6 is preferably protected by a bottom cover 50. The bottom cover 50 has two longitudinal sides and two lateral sides. One side of the bottom cover 50 defines the loading system passageway 52. The loading system passageway 52 has a spring loaded cover 54 that pivots below the loading system 8 when the loading system 8 is in the external station 94 and covers the loading system passageway 52 when the loading system 8 is in the sampling station. The loading system passageway cover 54 protects the inside of the electrophoresis instrument 6 from potential external disruptions such as particulate matter, wind, stray light, etc. The electrophoresis system 6 has support legs 56. The electrophoresis instrument 6 has a top hood 58 that covers analytical equipment. The top hood 58 is hinged to allow for easy access to the analytical equipment.

Figure 4:
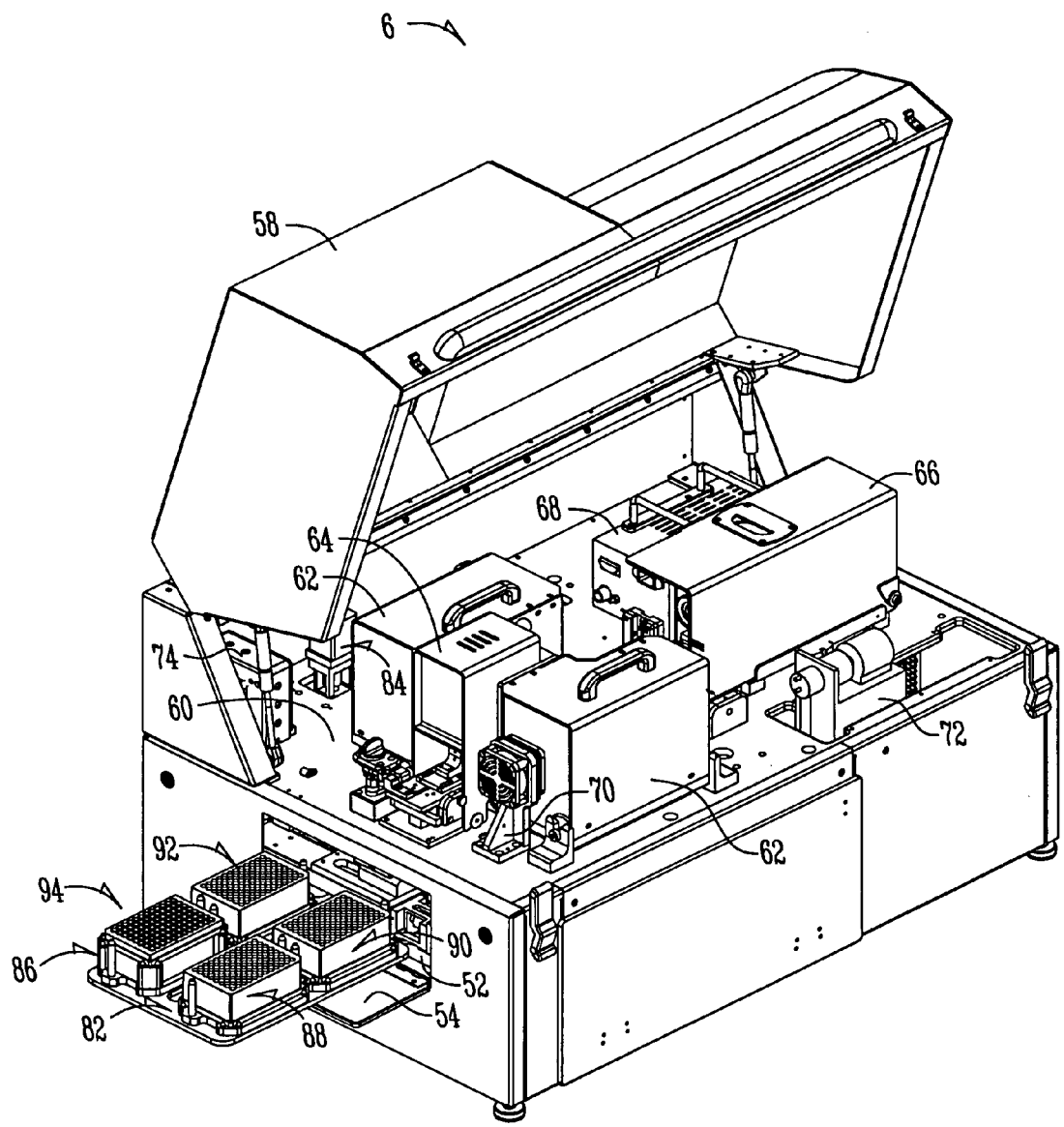
FIG. 4 presents a perspective view of the electrophoresis instrument having a loading system in an external station with the top cover raised.

FIG. 4 illustrates the electrophoresis instrument 6 with the top hood 58 in an open position. In this position is seen a top tooling plate assembly or instrument body 60 that is preferably a rigid horizontal surface forming a plane with an x-axis or lateral axis and a y-axis or longitudinal axis. The instrument body 60 has points of attachment on both its top surface and its lower surface. The instrument body 60 has attached a capillary array container (CAC) box 62, a lamp slide assembly 64, and a optics slide rail assembly 66. Further seen on the instrument body, is the CAC box power supply 68, a cooling fan 70 for the CAC box 62, and a lamp power supply 74. A pump 72 is also seen extending through a portion of the instrument body 60. The CAC box houses the circuit board 32 and the array block 18 as seen in FIG. 3.

As further seen in FIG. 4, the loading system 8 has components exposed when the loading system passageway cover 54 is open. The carriage 82 extends through the loading system passageway 52. Under the top cover 58 is the tray elevator 84. The carriage 82 is preferably approximately parallel with the instrument body 60 and moveably in the lateral and longitudinal directions. The tray elevator 84 is preferably approximately perpendicular with the instrument body 60 and moveable orthogonally relative to the instrument body 60.

Trays 30 are positioned in up to four positions upon the carriage 82. Trays 30 may be shallow or deep. Preferably, there are four positions for trays 30. A carriage first position 86 is typically reserved for a tray 30 holding a sample. As seen in FIG. 4, a shallow tray 30 is in carriage first position 86. A carriage second position 88 is typically reserved for a tray 30 holding buffer. As seen in FIG. 4 a deep tray 30 is in carriage second position 88. A carriage third position 90 is typically reserved for a tray 30 for receiving waste. A carriage fourth position 92 may be used for a tray 30 to hold sample, to hold sample, or to receive waste. All four carriage positions may be easily reached when in the external station 94 by a robot positioned outside the instrument 6.

Figure 5:
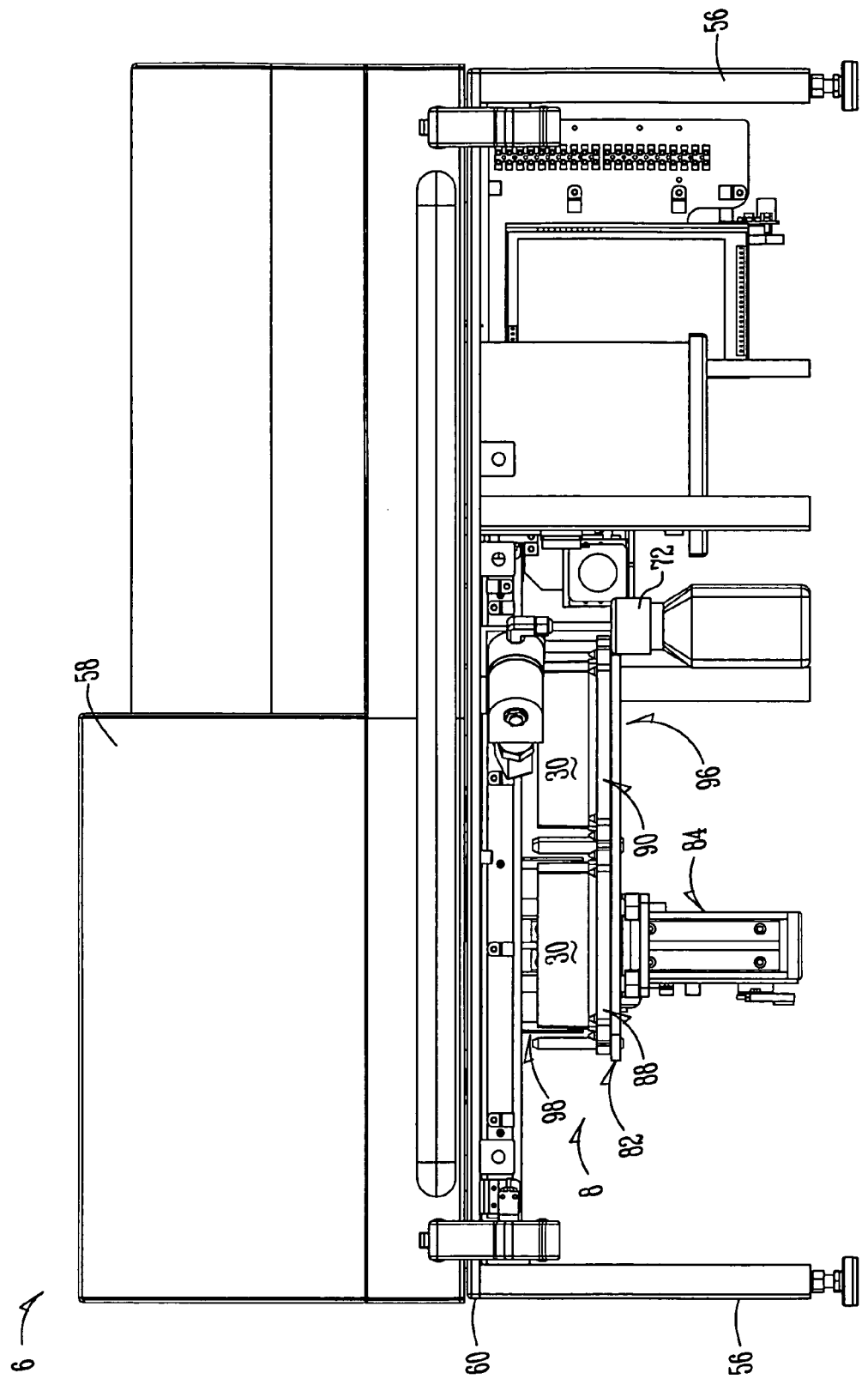
FIG. 5 presents a front view of the electrophoresis instrument without a bottom cover having a loading system at an internal station.

FIG. 5 illustrates a front view of the electrophoresis instrument 6 without the bottom cover 50 and having the top cover 58 closed. The support legs 56 are supporting the electrophoresis instrument 6 at the four corners of the instrument body 60. The support legs 56 are preferably extending the instrument body up a sufficient distance from a resting surface for clearance of the tray elevator 84 and other instruments attached to the instrument body 60. As seen in this figure, the carriage 82 is positioned at the internal station 96 and the tray 30 at the carriage first position (not seen) located at a sampling station 98. As further seen in this figure, there is sufficient longitudinal clearance about sampling station 98 such that the carriage 82 if moved longitudinally along the y-axis will not strike the bottom cover (not shown).

Figure 6:
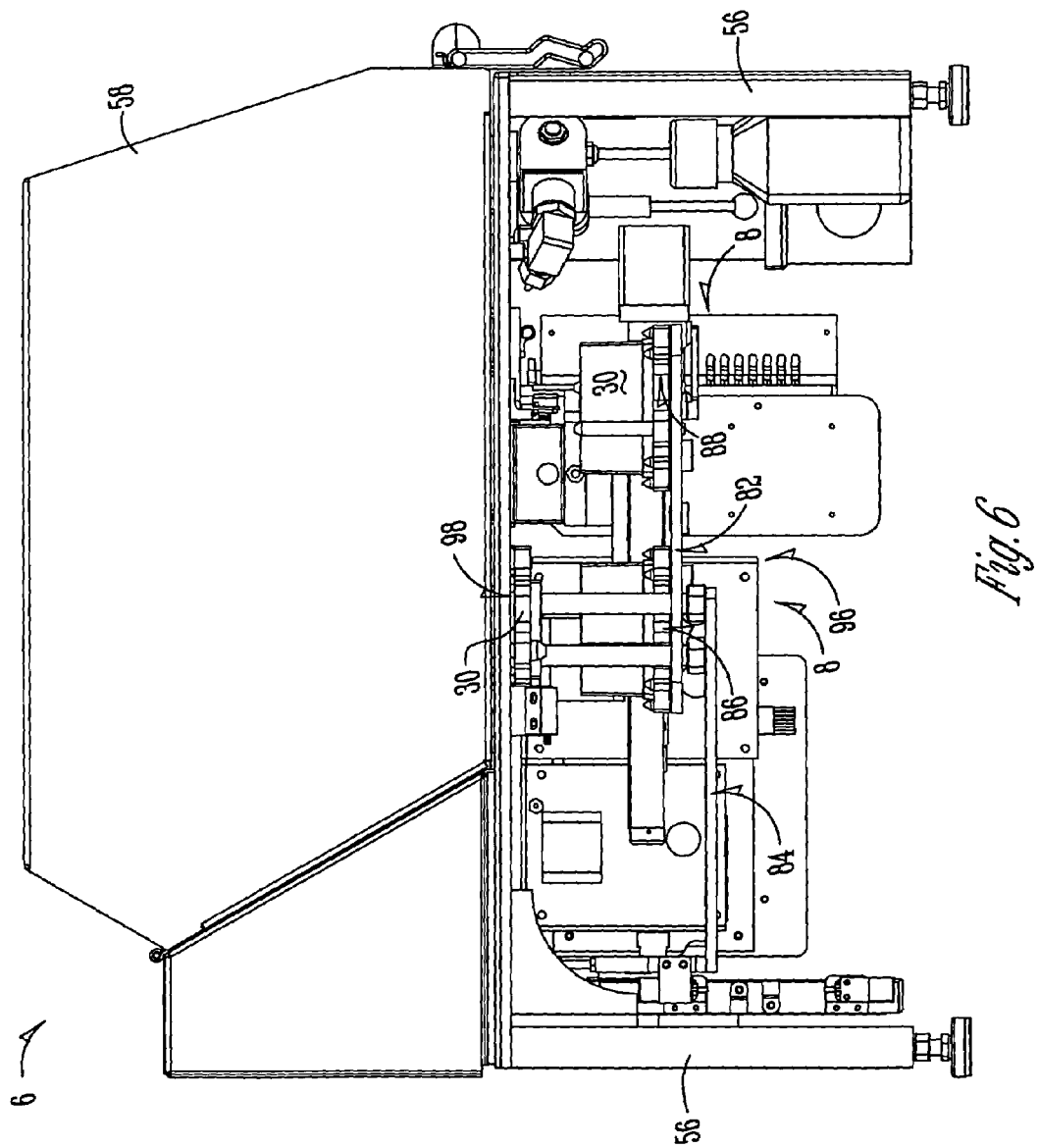
FIG. 6 presents a side view of the electrophoresis instrument having a loading system at an internal station.

FIG. 6 presents a side view of the electrophoresis instrument 6 having the loading system at an internal station 96. As seen in this figure, the carriage 82 is positioned at the internal station 96 and the tray 30 located at carriage first position 86. The tray 30 is lifted by the tray elevator 84 into position at the sampling station 98. As further seen in this figure, there is sufficient lateral clearance about sampling station 98 such that the carriage 82 if moved laterally along the x-axis will not strike the bottom cover (not shown).

Figure 7:
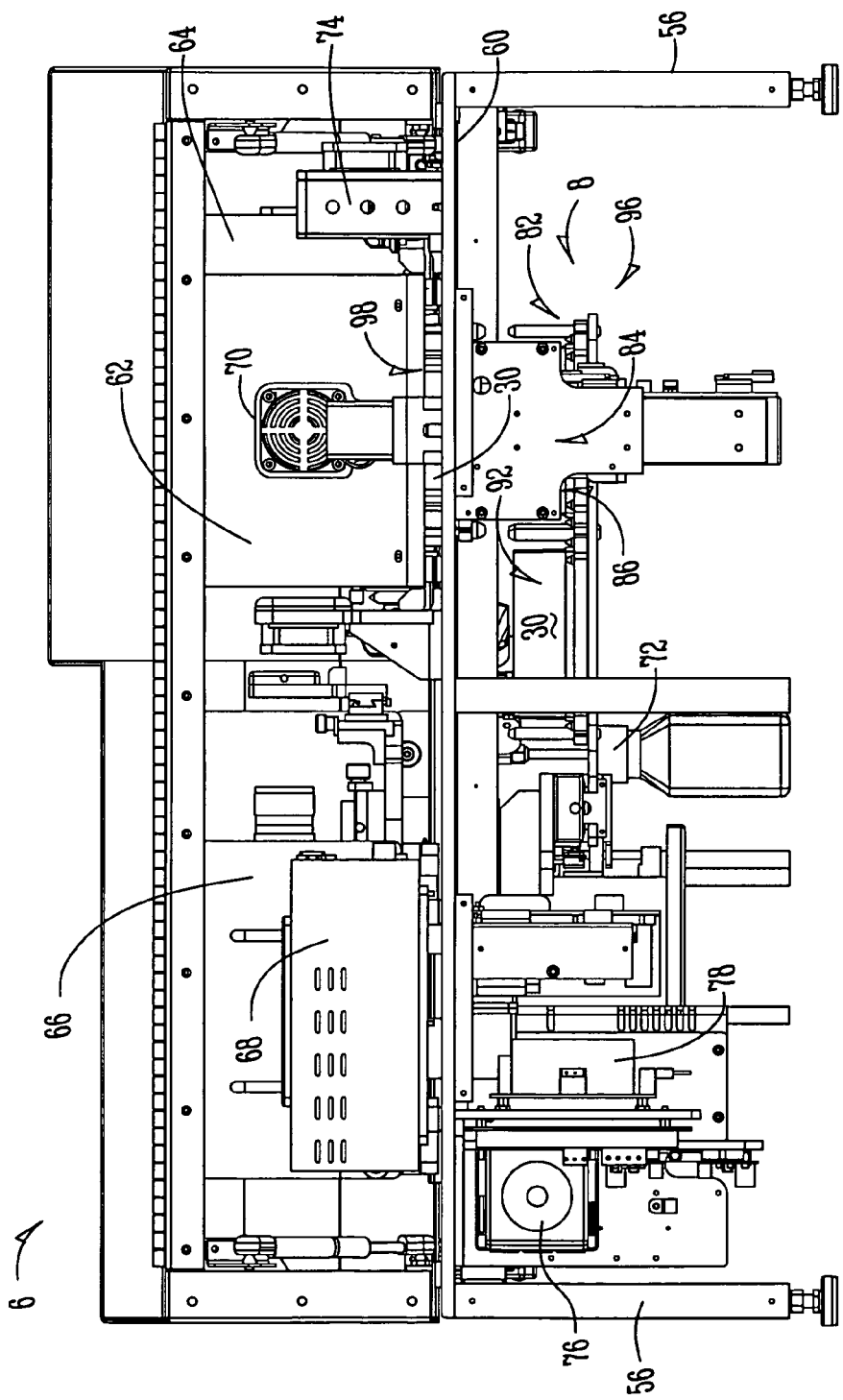
FIG. 7 presents a back view of the electrophoresis instrument having a loading system at an internal station with the tray elevator in the up position.

FIG. 7 illustrates a back view of the electrophoresis instrument 6 without the bottom cover 50 and having the top cover 58 closed. As seen in this figure, the carriage 82 is positioned at the internal station 96 and the tray 30 at the carriage first position 86 located at a sampling station 98. The tray elevator 84 is elevating the tray 30 so that it comes into contact with the CAC box 62 for sampling.

Further seen in FIG. 7 is the preferred general positioning of electrophoresis instrument components, including: CAC box 62, lamp slide assembly 64, optics slide rail assembly 66, CAC box power supply 68, CAC cooling fan 70, reservoir drain assembly 72, control board assembly 76, lamp power supply 74 and control circuit board assembly 78. These components are positioned such that they do not interfere with the mechanical operation of the loading system 8.

Figure 8:
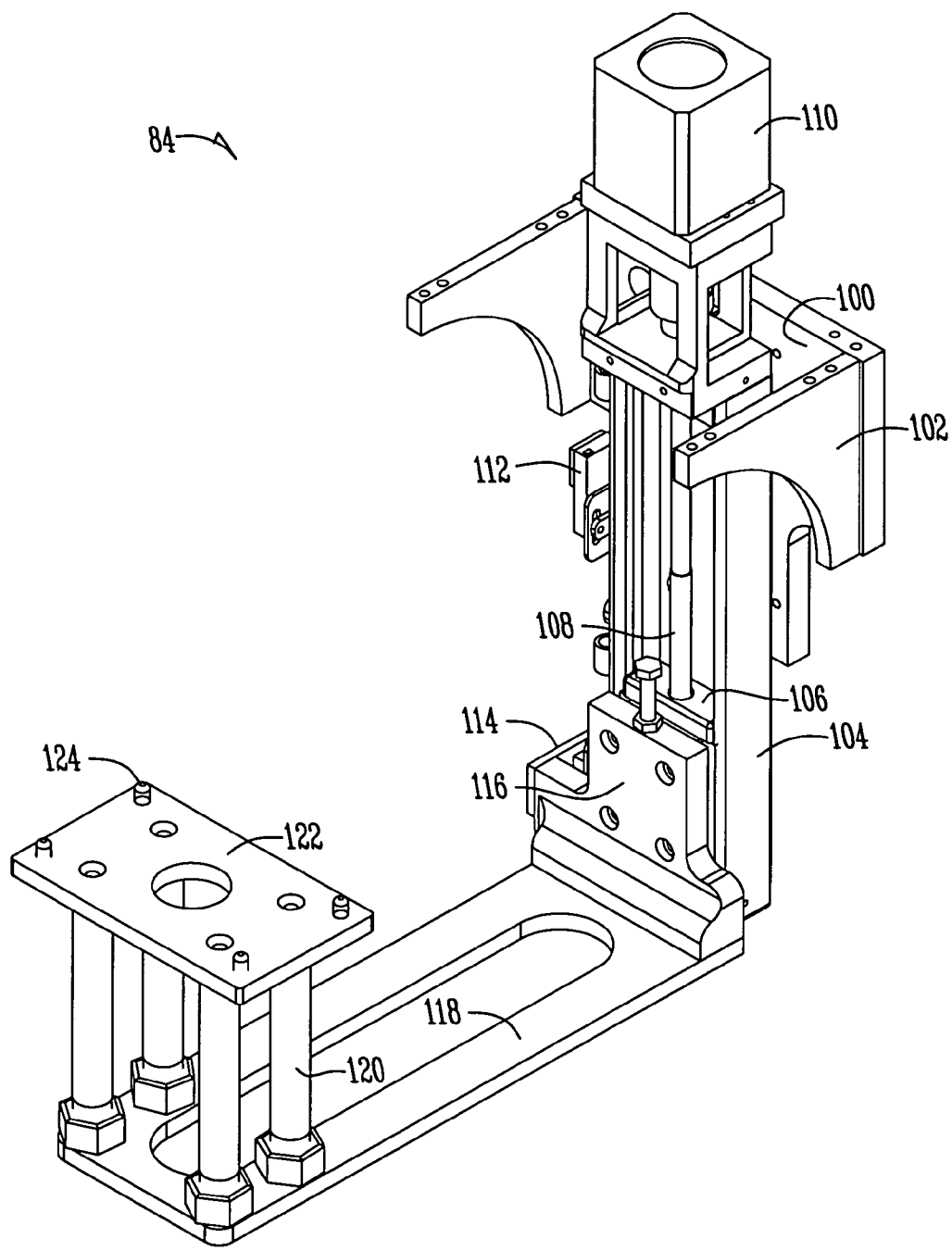
FIG. 8 presents a perspective view of the tray elevator.

FIG. 8 illustrates the tray elevator 84. The tray elevator 84 has a mounting plate 100 for attaching to the instrument body 60. The mounting plate 100 has two mounting plate gussets 102 attached. The z-axis rail 104 is attached to the mounting plate 100. A z-axis bearing 106 is slidably mounted within the z-axis rail 104. A stepper motor 110 is in axial alignment with the z-axis bearing 106 and attached to the z-axis bearing by a threaded shaft 108. The stepper motor 110 moves the tray 30 to an upper limit as determined by the upper sensor 112 and to a lower limit determined by a lower sensor 114.

A lift platform mounting plate 116 is attached to the z-axis bearing 106. An arm plate 118 extends laterally from the z-axis rail 104 and is connected to the lift platform mounting plate 116. Extension pins 120 are connected to the lift platform and extend orthogonally away from the arm plate 118. On top of the extension pins is attached a pad platform 122. The pad platform has dowel 124 for joining with tray 30.

Figure 9:
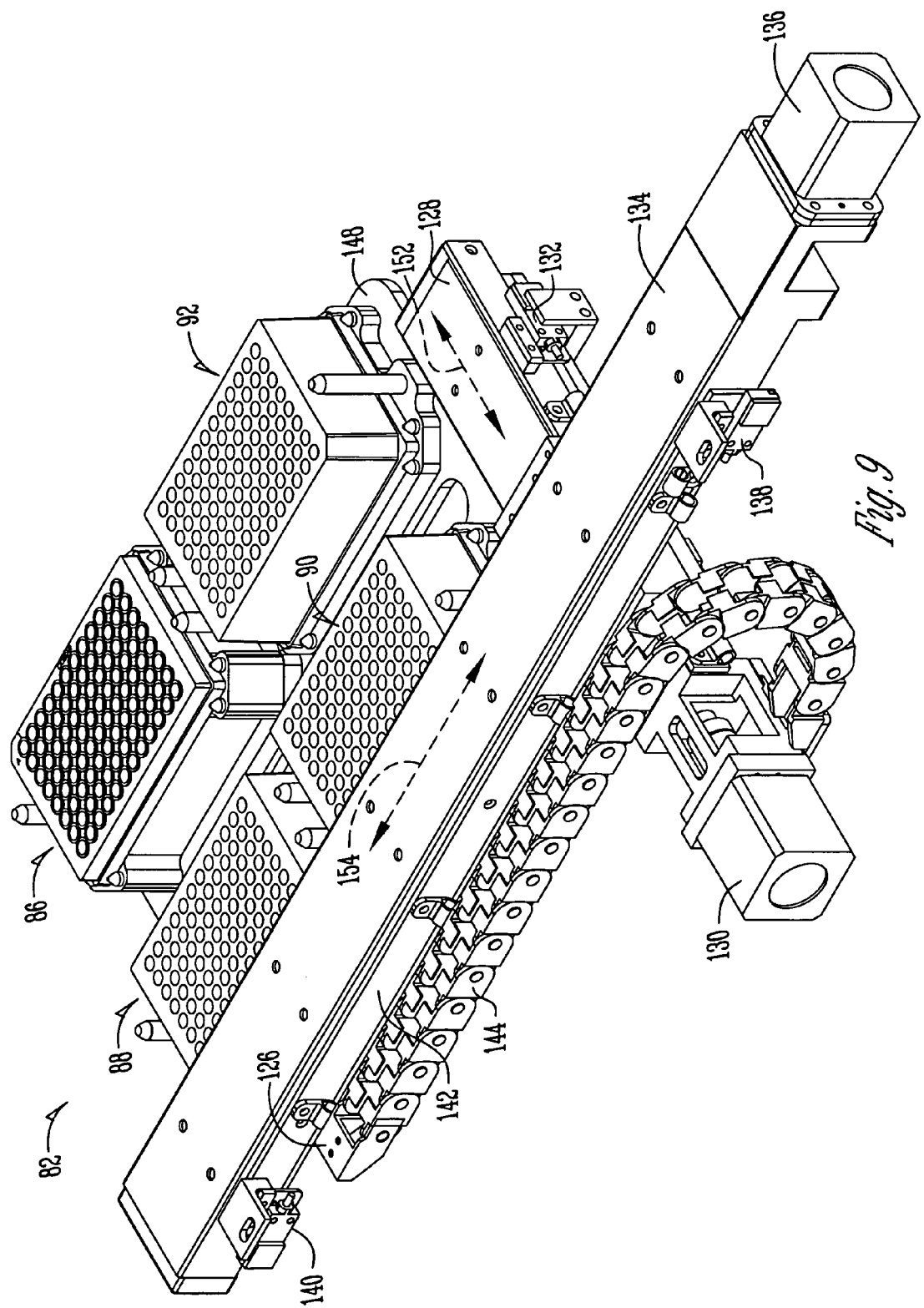
FIG. 9 presents a perspective view of the carriage and its mechanical actuators.

FIG. 9 illustrates the carriage 82. The tray carriage 82 has an y-axis rail 128. The y-axis bearing (not shown) is slidably mounted within the y-axis rail 128 to travel along line 152. A stepper motor 130 is in axial alignment with the y-axis bearing and attached to the y-axis bearing by a shaft. The stepper motor 130 moves the carrier 82 laterally to predetermined carriage positions established by first sensor (not shown) and second sensor 132.

The tray carriage has a x-axis rail 134. The x-axis bearing (not shown) is slidably mounted within the x-axis rail 134 to travel along line 154. The x-axis rail 134 is attached to the underside of instrument body 60. A stepper motor 136 is in axial alignment with the x-axis bearing and attached to the x-axis bearing by a shaft (not shown). The stepper motor 136 moves the carrier 82 longitudinally to predetermined carriage positions established by first sensor 138 and second sensor 140. A rail bar is attached to the x-axis rail. A cable management track 144 is attached to the instrument body 60 at mounting 126 and curls as the stepper motor 136 moves the carriage 82 to predetermined carriage positions.

Also seen in FIG. 9 is the sample tray platform plate 148. The sample tray platform 148 is attached to the y-axis bearing (not shown) within the y-axis rail 128. The y-axis rail 128 is attached to the x-axis bearing (not shown) within the x-axis rail 134.

Figure 10:
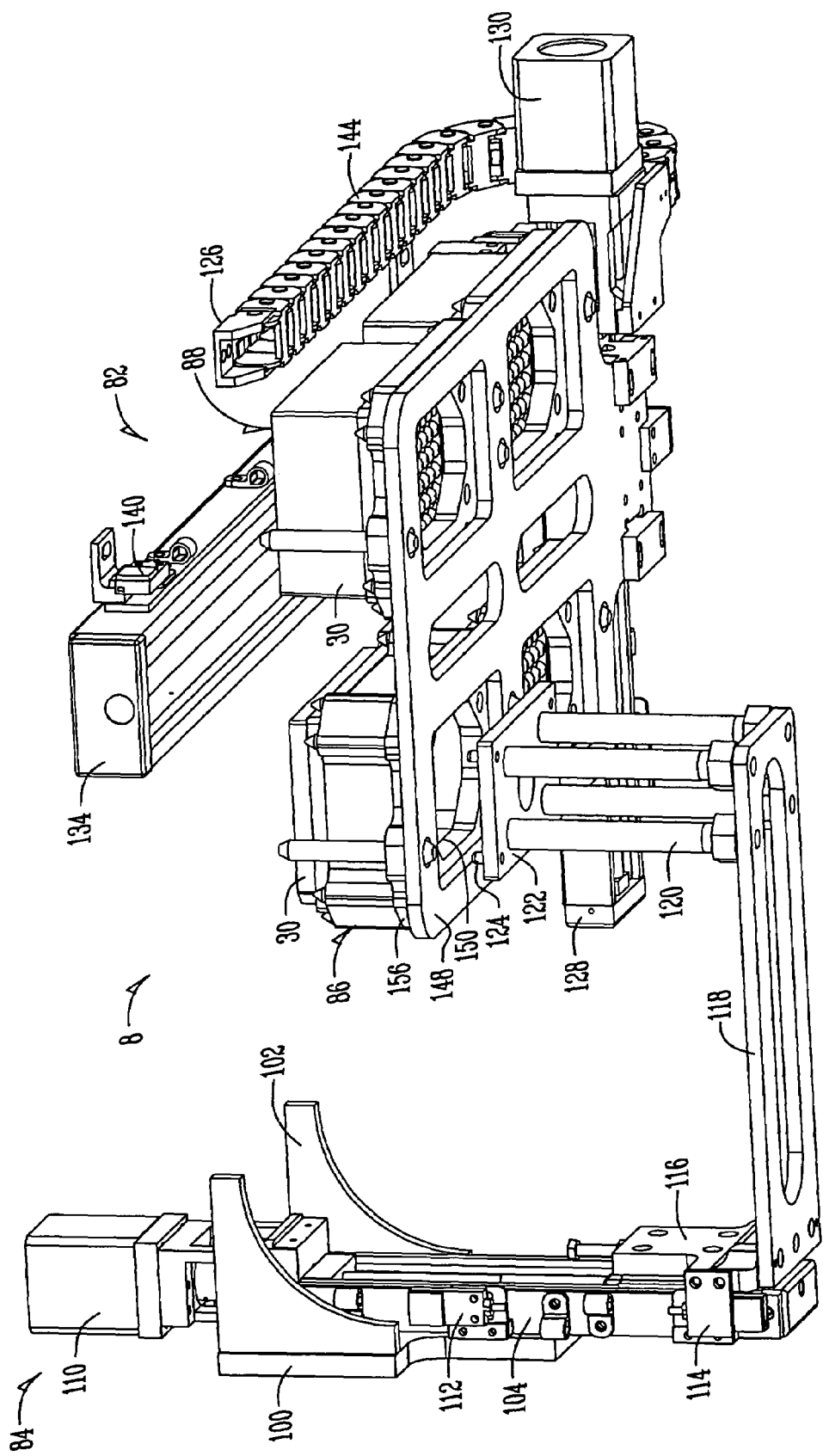
FIG. 10 presents a perspective view of the loading system without the instrument body with the tray elevator positioned under a first tray.

As seen in FIG. 10, the sample tray platform plate 148 defines passageways 150 so that the tray elevator 84 may lift a tray 30 from carriage positions 86, 88, 90, 92 and into the sampling station 98 at the CAC box 62.

FIGS. 1, 10, 11, and 12 illustrate the loading system 8 in use with an electrophoresis instrument 6.

As seen in FIG. 1, the loading system 8 has its carriage 82 extending outside the bottom cover 50 at an external station 94. At this point, the loading system 8 is presented to be loaded with trays 30 and/or unloaded with trays 30. The trays 30 may be manually placed upon the sample tray platform plate 148 or they may be placed with a robot (not shown).

Once loaded, the loading system 8 retracts the carriage 86 to the internal station 96. As seen in FIG. 10, the internal station 96 is achieved when the carriage is moved to a predetermined carriage position acknowledged by the x-axis first sensor 138. At this point, the carriage 82 may be in alignment with the sampling station 98; however, additionally the carriage 82 may be moved to a predetermined carriage position acknowledged by the y-axis first sensor (not shown).

As further seen in FIG. 10, at this point the tray elevator 84 has a pad platform 122 directly underneath the tray alignment plate 156 that is in the carriage first position 86. The tray alignment plate 156 may then be lifted by the tray elevator 84 engaging its stepper motor 110 and moving the pad platform 122, having the pad platform 122 contact the tray alignment plate 156 so that dowels 124 engage the underside of the tray alignment plate 156, and having the pad platform 122 along with the tray travel to a predetermined sampling position 98 adjacent the CAC box 62 acknowledged by the z-rail upper sensor 112. The CAC box then processes the contents in the tray 30 by a process previously described and illustrated in FIGS. 2 and 3.

Once the sample has been analyzed, the z-rail stepper motor 110 is engaged in an opposite direction and the pad platform and tray 30 travel downward through the sample tray platform plate 148. The tray alignment plate 156 is redeposited on the sample tray platform plate 148. The downward movement is then stopped at a predetermined position acknowledged by the z-rail lower sensor 114.

Figure 11:
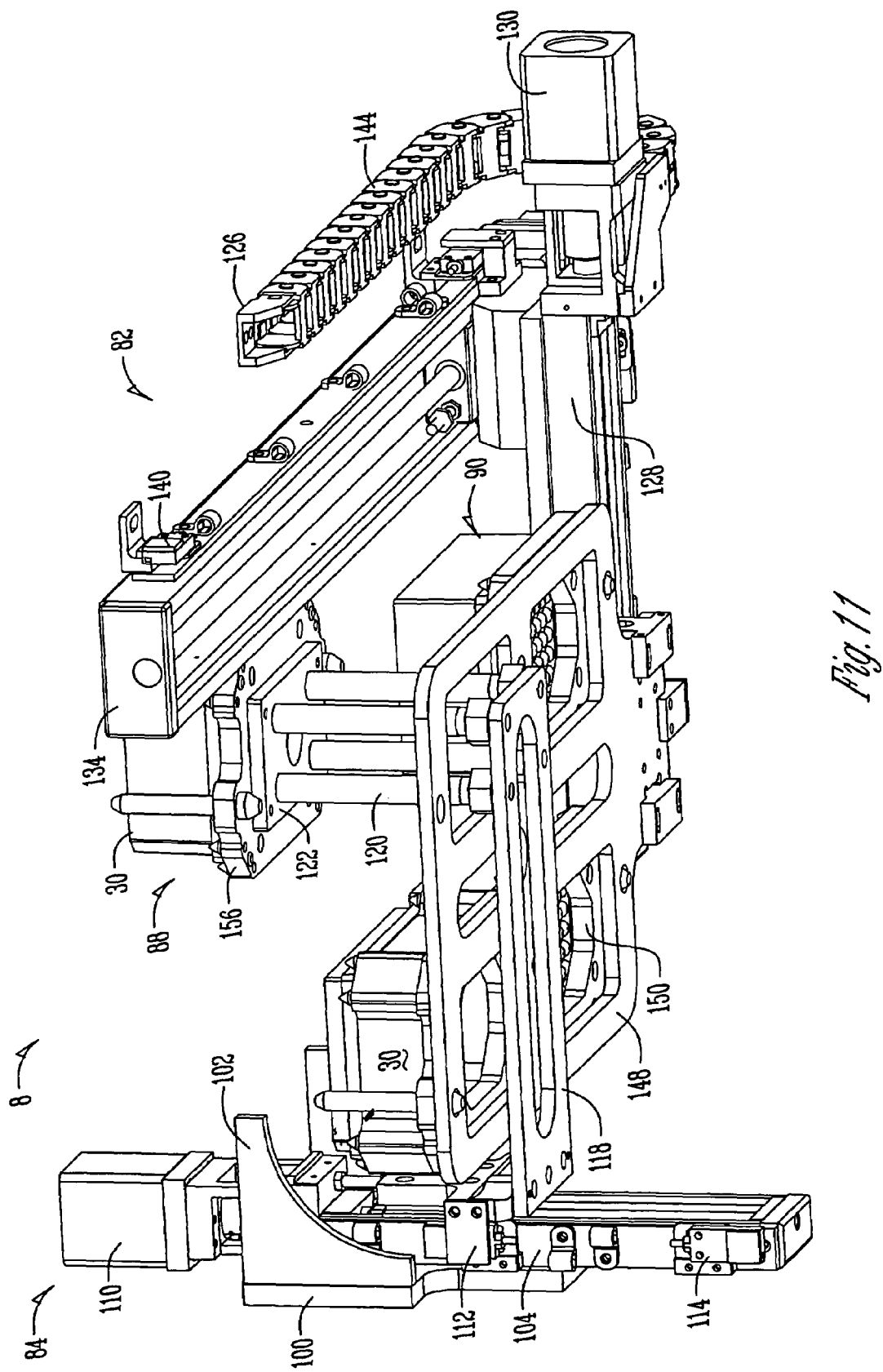
FIG. 11 presents a perspective view of the loading system without the instrument body with the tray elevator moving the second tray into a sampling station.

As seen in FIG. 11, the loading system 8 shows the tray 30 in carrier second position 88 in position at the sampling station 98. Sampling station 98 was achieved from the carrier first position 86 as seen in FIG. 10 by engaging the y-axis stepper motor 130 to a predetermined position indicated by the y-axis second sensor 132 and then engaging the z-axis stepper motor 110 such that the pad platform 122 extends through the sample tray platform plate 148 to connect with the sample tray alignment plate 156 to place in the sampling station 98. The CAC box 62 then processes the contents in the tray 30 by a process previously described and illustrated in FIGS. 2 and 3. Once the sample has been analyzed, the z-rail stepper motor 110 is engaged in an opposite direction and the pad platform and tray 30 travel downward through the sample tray platform plate 148. The tray alignment plate 156 is redeposited on the sample tray platform plate 148. The downward movement is then stopped at a predetermined position acknowledged by the z-rail lower sensor 114.

Figure 12:
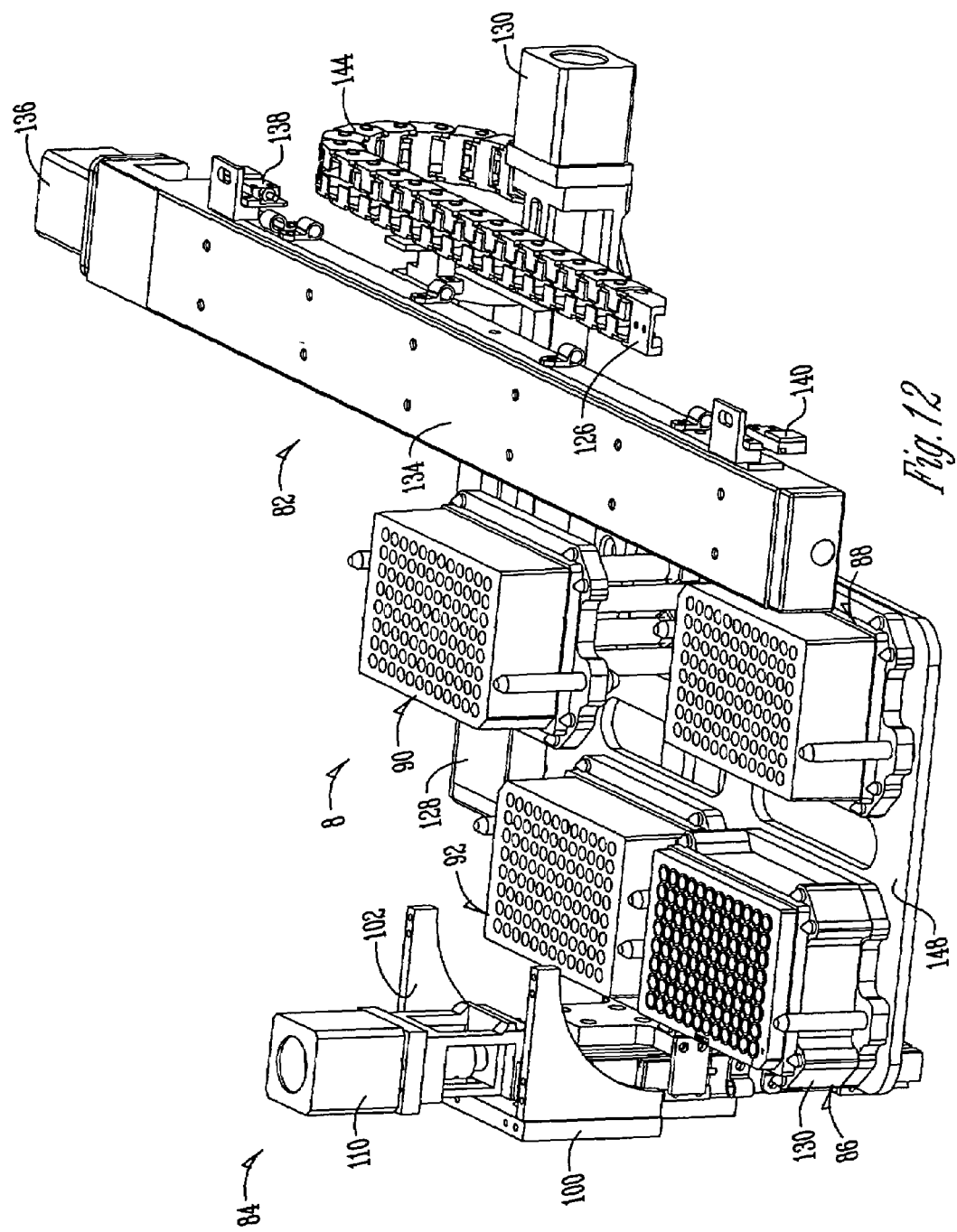
FIG. 12 presents a perspective view of the loading system without the instrument body with the tray elevator moving the third tray into a sampling station.

As seen in FIG. 12, the loading system 8 shows the tray 30 in carrier third position 90 at the sampling station 98. Sampling station 98 was achieved by engaging the x-axis stepper motor 136 to a predetermined position indicated by stepper motor revolution counts and then engaging the z-axis stepper motor 110 such that the pad platform 122 extends through the sample tray platform plate 148 to connect with the sample tray alignment plate 156 to place in the sampling station 98. The CAC box 62 then processes the contents in the tray 30 by a process previously described and illustrated in FIGS. 2 and 3. Once the sample has been analyzed, the z-axis stepper motor 110 is engaged in an opposite direction and the pad platform 122 and tray 30 travel downward through the sample tray platform plate 148. The tray alignment plate 156 is redeposited on the sample tray platform plate 148. The downward movement is then stopped at a predetermined position acknowledged by the z-rail lower sensor 114.

The loading system 8 may move the tray 30 in carrier fourth position 92 to the sampling station 98 from the carrier third position 90. This may be achieved by engaging the y-axis stepper motor 130 to a predetermined position indicated by the x-axis first sensor (not shown) and then engaging the z-axis stepper motor 110 such that the pad platform 122 extends through the sample tray platform plate 148 to connect with the sample tray 30 to place in the sampling station 98. The CAC box 62 then processes the contents in the tray 30 by a process previously described and illustrated in FIGS. 2 and 3. Once the sample has been analyzed, the z-axis stepper motor 110 is engaged in an opposite direction and the pad platform 122 and tray 30 travel downward through the sample tray platform plate. The tray alignment plate 156 is redeposited on the sample tray platform plate 148. The downward movement is then stopped at a predetermined position acknowledged by the z-rail lower sensor 114.

In use, a variety of different combinations of sampling trays may be configured for alternating between different samples, different buffers, and/or waste receiving. The above progression from carriage first position 86, carriage second position 88, carriage third position 90, and carriage fourth position 92 is an illustration of the movement achieved by differing combinations of stepper motor movements.

In use, sample may be provided by either a deep tray 30 or a shallow tray 30. Mechanically the electrophoresis instrument 6 functions similarly for either tray style used.

Figure 13:
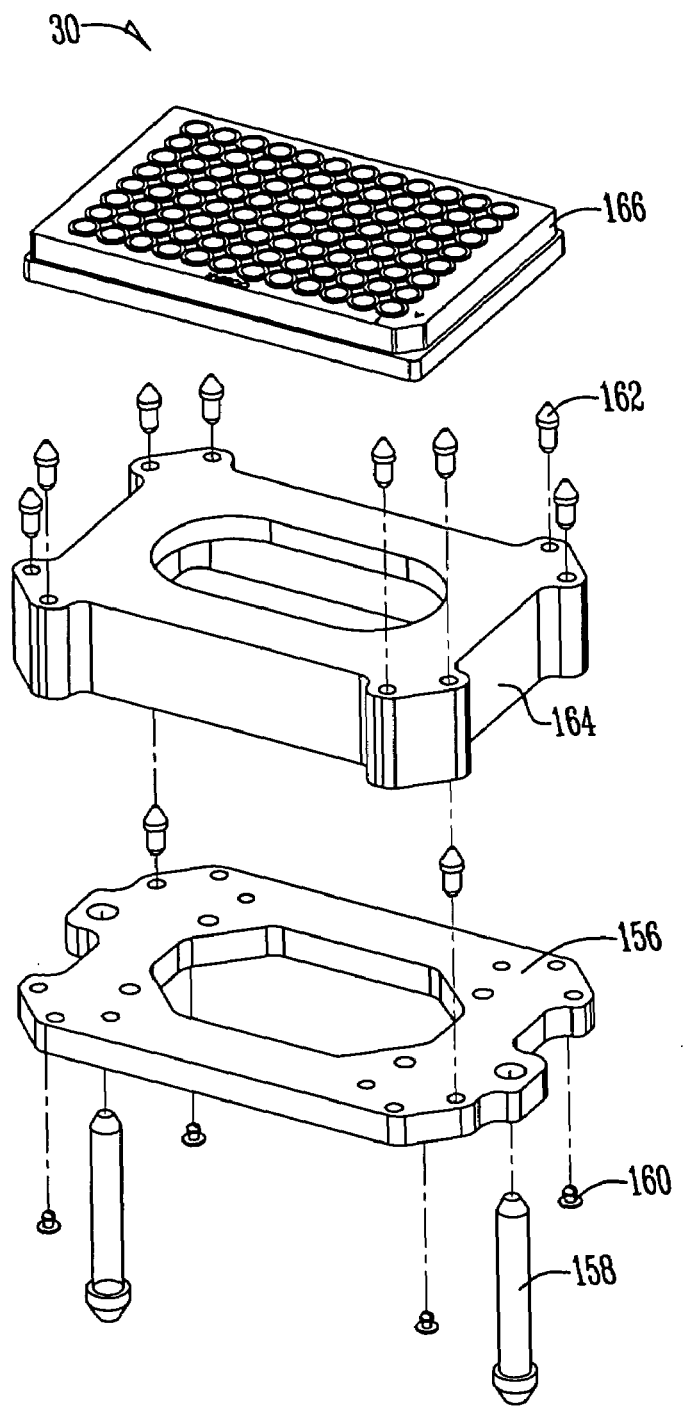
FIG. 13 presents an exploded view of a shallow tray, spacer, and alignment plate.

FIG. 13 illustrates an exploded view of a shallow well tray 30. The shallow well tray 30 has a tray alignment plate 156. Tray carrier alignment pins 158 extend through the tray alignment plate 156. Rest button rivets 160 attach to the bottom of the tray carrier alignment plate for contact with the pad platform 122. A shallow well spacer 164 is in parallel alignment with the tray alignment plate 156 and connected by lower alignment button 162. A microplate shallow well 166 is in parallel alignment and positioned by alignment buttons 162 to the shallow well spacer 164. The microplate deep well 168 is preferably made of an inert material such as polytetrafluoroethylene, polyethylene, polypropylene or polyethylene terephthalate.

Figure 14:
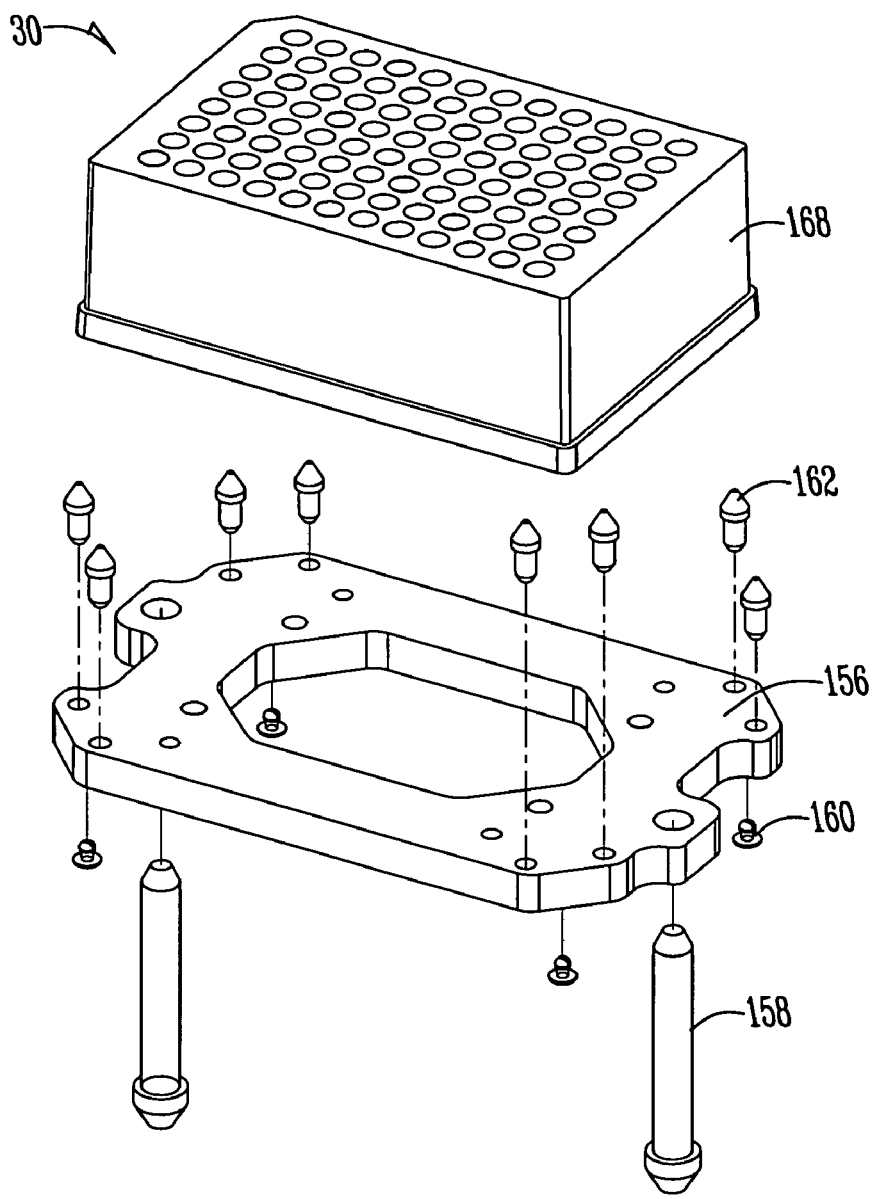
FIG. 14 presents an exploded view of a deep tray and alignment plate.

FIG. 14 illustrates an exploded view of a deep tray 30. The deep tray 30 has a tray alignment plate 156. Tray carrier alignment pins 158 extend through the tray alignment plate 156. Rest button rivets 160 attach to the bottom of the tray carrier alignment plate for contact with the pad platform 122. A microplate deep well 168 is in parallel alignment and positioned by alignment buttons 162. The microplate deep well 168 is preferably made of an inert material such as polytetrafluoroethylene, polyethylene, polypropylene or polyethylene terephthalate.

As seen in FIG. 13 and FIG. 14, the shallow tray and the deep tray when assembled are the same height. The shallow well spacer 164 is designed such that the shallow tray is the same height as the deep tray. By having the shallow tray the same height as the deep tray, the z-axis upper sensor 112 does not need to be adjusted when replacing a shallow tray for a deep tray or replacing a deep tray for a shallow tray.

The addition of a loading system that is moveable between an external station and a sampling station as described allows for high throughput through robotic interface capabilities and stand alone operation. The loading system has a carriage that in the external station is robotic friendly. By "robotic friendly," the applicant means that the carriage is accessible by a robot for the addition, removal, and/or the manipulation of trays. Along with many advantages of using a robot, the robot provides accuracy and efficiency of movement that contribute to high throughput analysis. The addition of a loading system also allows for stand alone operation as the loading system may contain more than one tray containing sample, buffer, and/or waste. The loading system containing these trays has stand alone operation as a human operator does not need to interface with the instrument once trays have been placed upon the carriage.

In the drawings and specification, there has been set forth a preferred embodiment of the invention, and although specific terms are employed, these are used in a generic descriptive sense only and not for purposes of limitation. Changes in the form and the proportion of parts as well as in the substitution of equivalents are contemplated as circumstance may suggest or render expedient without departing from the spirit or scope of the invention in the following claims.

What is claimed is:

1. An electrophoresis instrument, the instrument comprising:
    an instrument body;
    a carriage attached to the instrument body moveable between an external station and an internal sampling station;
    at least one tray upon the carriage;
    an array of capillary tubes attached to the instrument body sampling the tray at the sampling station;
    a photodetector attached to the instrument body for detecting light passing through the capillary tubes; and
    a light source attached to the instrument body positioned with respect to the photodetector.

2. The system of claim 1 further comprising a tray elevator attached to the instrument body moveable between a carriage station and the sampling station.

3. The system of claim 2 wherein the carriage is further capable of lateral movement between a plurality of internal stations.

4. The system of claim 3 wherein the carriage is further capable of longitudinal movement between the plurality of internal stations.

5. The system of claim 1 wherein the tray includes a shallow reservoir body connected to a spacer body.

6. The system of claim 1 wherein the tray is a deep reservoir body.

7. The system of claim 1 wherein the carriage is longitudinally moveable between the external station and the sampling station.

8. The system of claim 1 wherein the external station is accessible by a robotic positioning tool.

9. A loading system for an electrophoresis instrument, the loading system comprising:
   a carriage moveable between an external station and an internal sampling station, the carriage moveable along a passageway;
   a closeable cover attached to the electrophoresis instrument that closes the passageway when the carriage is at the internal sampling station to protect the electrophoresis instrument from external disruptions;
   at least one tray upon the carriage; and
   the sampling station adapted for sampling the tray by an array of capillary tubes.

10. The system of claim 9 further comprising a tray elevator moveable between a carriage station and the sampling station.

11. The system of claim 9 wherein the carriage is further capable of lateral movement between a plurality of internal stations.

12. The system of claim 9 wherein the carriage is further capable of longitudinal movement between the plurality of internal stations.

13. The system of claim 9 wherein the carriage is longitudinally moveable between the external station and the sampling station.

14. The system of claim 9 wherein the external station is accessible by a robotic positioning tool.

15. A method of using an electrophoresis instrument with a loading system, the method comprising:
    loading at least one tray upon a carriage at an external station;
    moving the carriage from the external station to an internal sampling station;
    sampling the tray with an array of capillary tubes;
    emitting light from a light source directed through the array of capillary tubes; and
    detecting light passing through the capillary tubes with a photodetector.

16. The method of claim 15 further comprising the step of elevating the tray with a tray elevator from a carriage station to a sampling station.

17. The method of claim 16 further comprising the step of laterally moving the carriage between a plurality of internal stations.

18. The method of claim 17 further comprising the step of longitudinally moving the carriage between the plurality of internal stations.

19. The method of claim 15 further comprising the step of longitudinally moving the carriage between the external station and the sampling station.

20. The method of claim 15 wherein the step of loading at least one tray upon a carriage at an external station is performed by a robot.

* * * * *